(12) United States Patent
Lee

(10) Patent No.: US 6,800,067 B2
(45) Date of Patent: Oct. 5, 2004

(54) TWO-COMPONENT SAFETY SYRINGE

(76) Inventor: Steve Lee, 3F, No. 18, Lane 9, Kangshan Rd., Peitou Dist., Taipei (TW)

( * ) Notice: Subject to any disclaimer, the term of this patent is extended or adjusted under 35 U.S.C. 154(b) by 16 days.

(21) Appl. No.: 10/327,012

(22) Filed: Dec. 24, 2002

(65) Prior Publication Data
US 2004/0122364 A1 Jun. 24, 2004

(51) Int. Cl.⁷ .............................................. A61M 5/00
(52) U.S. Cl. ....................................... 604/110; 604/192
(58) Field of Search ................................ 604/195, 192, 604/198, 187, 110, 263, 193, 194, 196, 197, 188, 264

(56) References Cited

U.S. PATENT DOCUMENTS 6,193,695 B1 * 2/2001 Rippstein, Jr. .............. 604/195

* cited by examiner

Primary Examiner—Manuel Mendez
(74) Attorney, Agent, or Firm—Rosenberg, Klein & Lee

(57) ABSTRACT

A safety syringe includes two major components; a barrel and a plunger; a needle hub engaged with the barrel and a plunger slid ably received in the barrel to engage with the needle hub and to retract the needle hub into the barrel. A V-shape groove formed a thin membrane surround the needle hub. The V-shape groove separates the needle hub and the barrel into two peripheries—an inner periphery of the barrel and an outer periphery of the hub. The inner periphery of the barrel and the outer periphery of the hub are thicker than the thin membrane. Multiple pyramidal blocks extended from the outer periphery of the hub facing outward to the barrel. Multiple triangular cutouts with V-shape groove edge defined in the inner periphery of the barrel respectively correspond to one of the multiple pyramidal blocks.

5 Claims, 6 Drawing Sheets

TWO-COMPONENT SAFETY SYRINGE

BACKGROUND OF THE INVENTION

1. Field of the Invention

The present invention relates to a safety syringe, and more particularly to a safety syringe having two main components only; the barrel and the plunger. It has a V-shape groove formed a thin membrane between the needle hub and the barrel. The thin membrane integrally formed between the inner periphery of the barrel and the outer periphery of the needle hub and some multiple pyramidal blocks extending from the needle hub periphery facing outward to the barrel. Thus, when the needle hub is pulled backward into the barrel by the plunger, the pyramidal blocks tear the thin membrane to facilitate the retraction of the needle hub into the barrel.

2. Description of Related Art

Numerous patents discussing different structures and means of preventing accidental damage to medical personnel by used syringes have already been introduced to the market. Reviewing the patents, most of them concern the means of how the needle is retracted into the barrel. However, in most of the information provided in the available patents, after the syringe is used, the paramedics either remove the needle from the needle hub to avoid accidental injury to the others or dispose of the needle hub in a sterilizing processor to prevent any infection by the injury via the needle.

Reviewing both approaches, either the person is quite easy to be hurt by the needle or the managing cost raised by purchasing the sterilizing or destructing processor.

To overcome the shortcomings, the present invention tends to provide an improved safety syringe to mitigate and obviate, the aforementioned problems.

SUMMARY OF THE INVENTION

The primary objective of the present invention is to provide an improved safety syringe to allow the medical personnel to safely retract the needle hub together with the needle in the barrel.

Another objective of the present invention is to provide an improved safety syringe that has a thin membrane formed between the barrel and the needle hub and multiple pyramidal blocks extended from the hub periphery, with two-side V-shape groove edge formed thin membrane. Therefore, when the needle hub is pulling backward into the barrel by the plunger, the pyramidal blocks destroy the thin membrane to allow the retraction of the needle hub into the barrel and thus the user's safety is secured.

Other objects, advantages and novel features of the invention will become more apparent from the following detailed description when taken in conjunction with the accompanied drawings.

DETAILED DESCRIPTION OF THE PREFERRED EMBODIMENT

Figure 1:
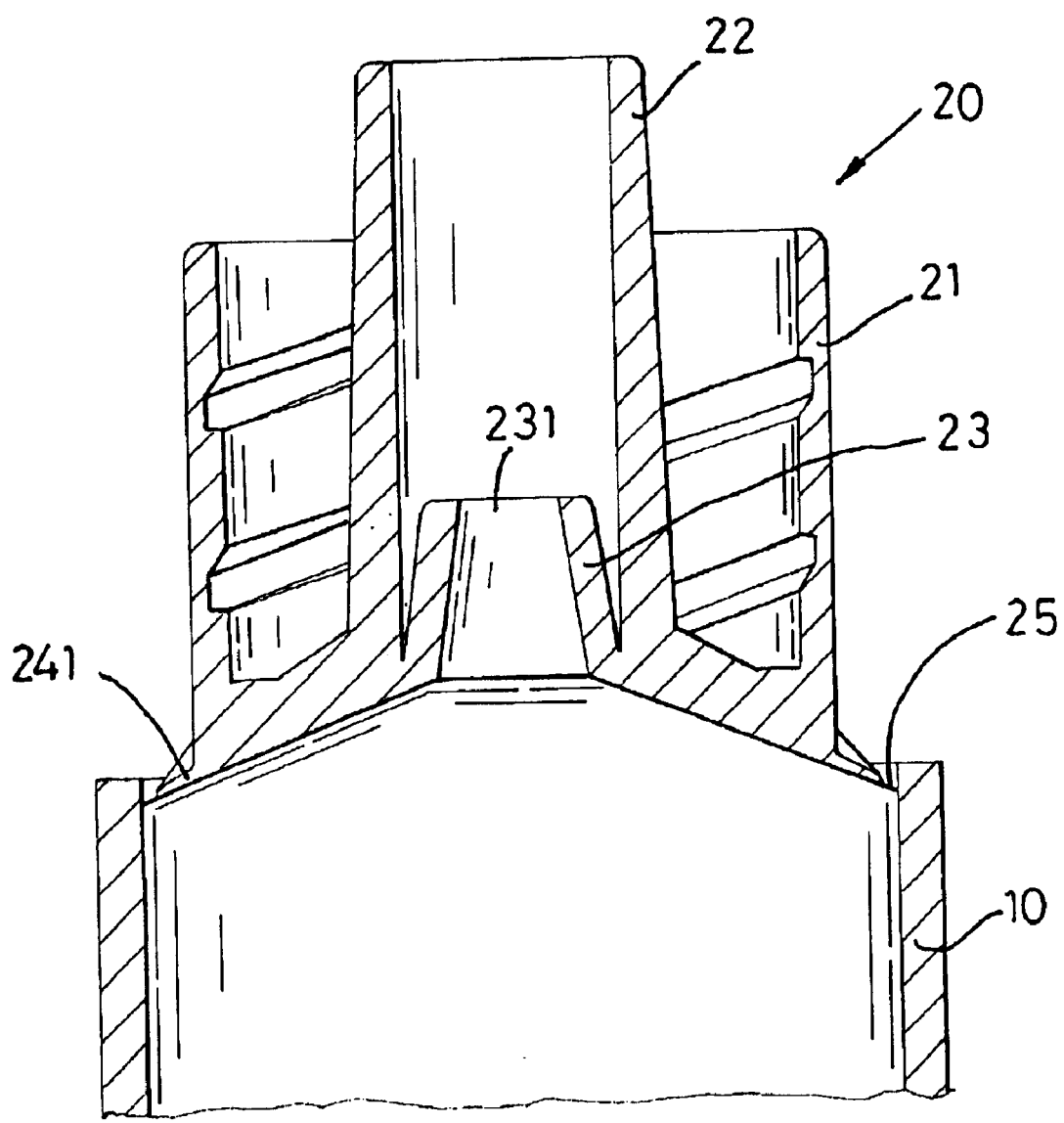
FIG. 1 is a cross sectional view of barrel and a needle hub of the present invention.
Figure 2:
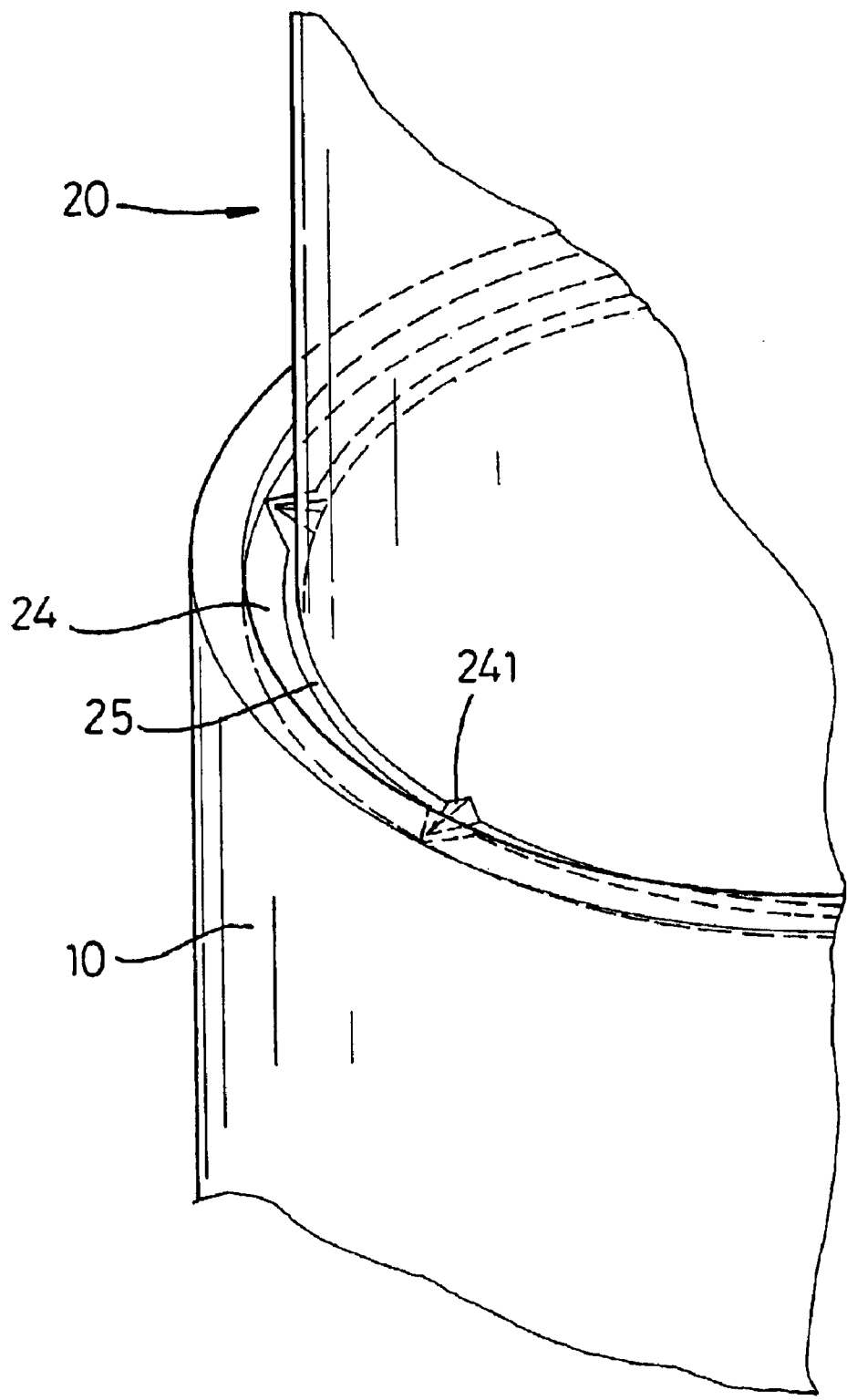
FIG. 2 is a partial perspective view of the needle hub and the barrel.

With reference to FIG. 1 and FIG. 2, the safety syringe in accordance with the present invention has a barrel (10) and a needle hub (20). The needle hub (20) has a first seat (21) and a second seat (22) integrally formed inside the first seat (21). A central seat (23) is also formed inside the second seat (22) and has a through hole (231) centrally defined in the central seat (23). An inner periphery of the barrel (24) integrally extends from the barrel (10). A thin membrane (25) is formed at the bottom of the V-Shape groove around the outer periphery of the needle hub (20) and connected to the inner periphery of the barrel (24).

Figure 3:
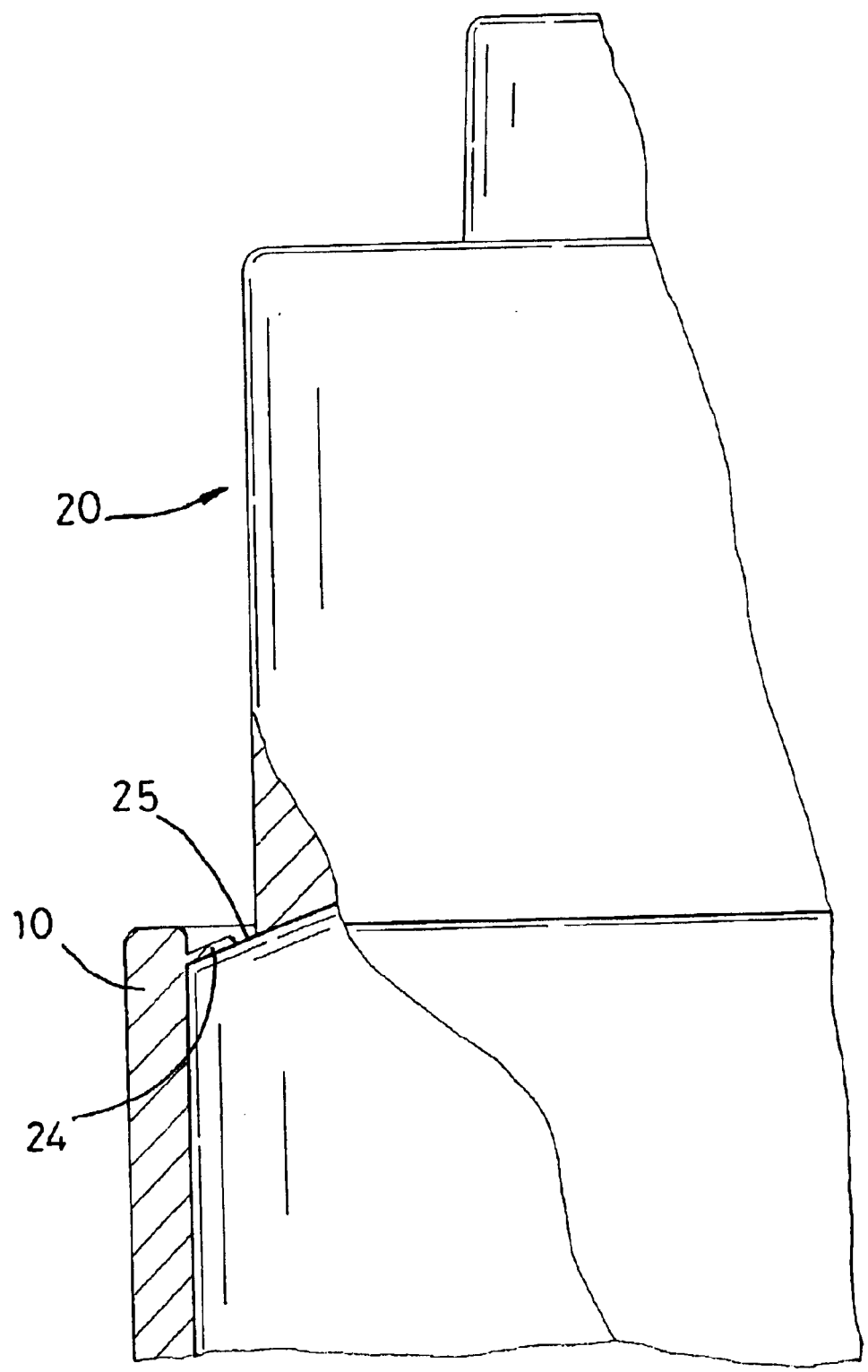
FIG. 3 is a sides plan view of the needle hub and the barrel in partial section showing a thin membrane is formed between the inner periphery of the barrel and the outer periphery of the needle hub.

With reference to FIG. 3, the inner periphery of the barrel (24) is thicker than that of the thin membrane (25).

Figure 4:
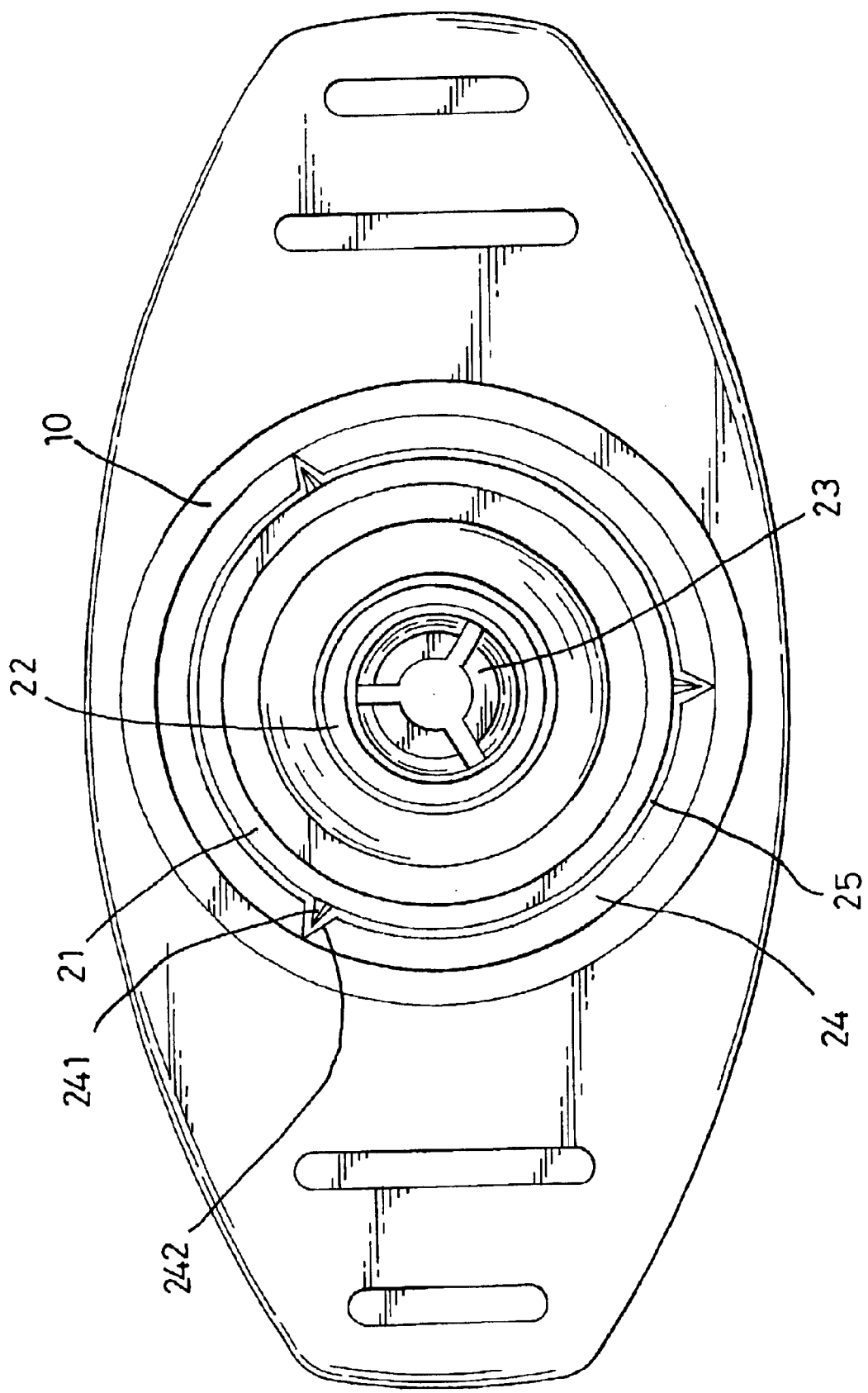
FIG. 4 is a top plan view of the needle hub and the barrel.

With reference to FIG. 4, the thin membrane (25) has multiple pyramidal blocks (241) extended from the hub periphery formed on atop surface of the thin membrane (25). Multiple triangular cutouts (242) are formed on the inner periphery of the barrel (24) to correspond to the multiple pyramidal blocks (241) and are V-shape grooved with the thin membrane (25). Therefore, each of the pyramidal blocks (241) is spaced away from the inner periphery of the barrel (10).

Figure 5:
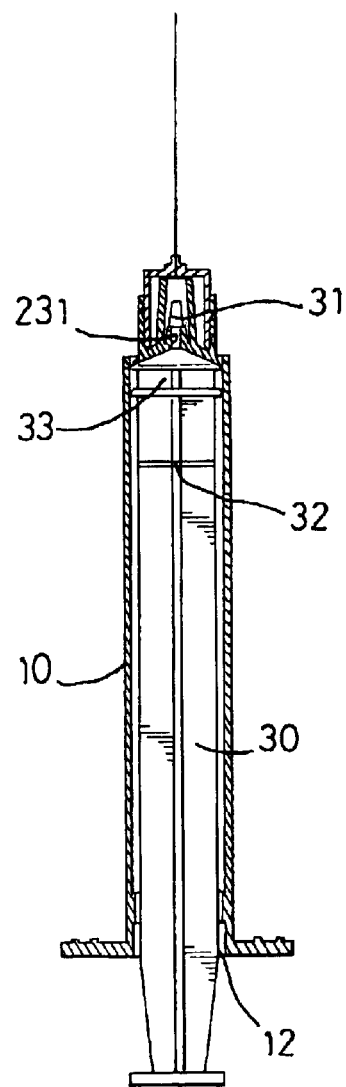
FIG. 5 is a schematic view showing the engagement of the plunger with the needle hub.
Figure 6:
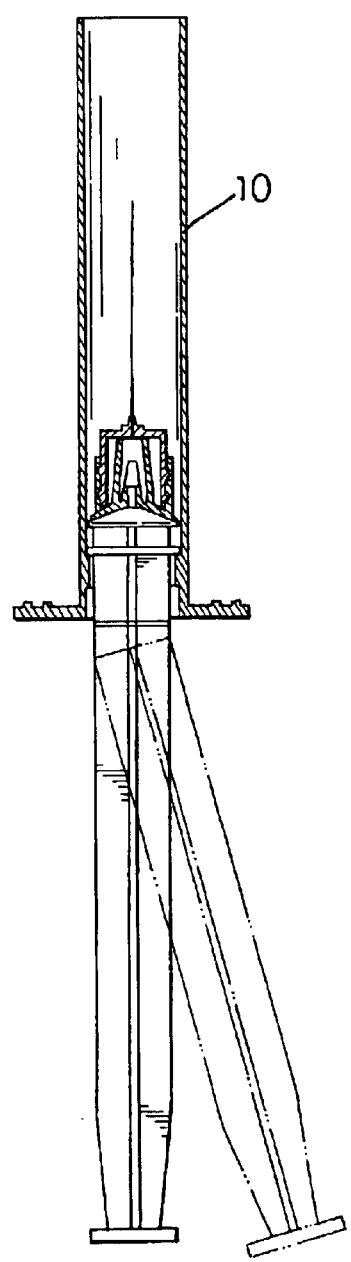
FIG. 6 is a schematic view showing that after the needle hub is pulled back into the barrel by the plunger, the user is able to break the linking rod of the plunger to retain the needle hub in the barrel.

With reference to FIGS. 5 and 6, a plunger (30) is slidably received in the barrel (10) from an opening (12) of the barrel (10) and has a hooking tip (31) formed on the distal end of the plunger (30), a linking rod (32) formed between a top portion and a bottom portion of the plunger (30) and a plug (33) sandwiched between a joint between the hooking tip (31) and the top portion of the plunger (30).

After the plunger (30) is inserted into the barrel (10) to inject the medicine received in the barrel (10), the user continues to push the plunger (30) into the needle hub (20) to extend through the through hole (231). Thus, the hooking tip (31) is able to securely engage with a peripheral edge of the through hole (231). Thereafter, the user retracts the plunger (30) and while pulling the plunger (30) backward, due to the secured engagement between the plunger (30) and the needle hub (20), the needle hub (20) is also driven to move inside the barrel (10). However, when the needle hub (20) is being driven to move inside the barrel (10), the pyramidal blocks (241) tear the thin membrane (25) to completely separate the needle hub (20) from the barrel (10), thus needle hub (20) will be retracted into the barrel (10).

Figure 7:
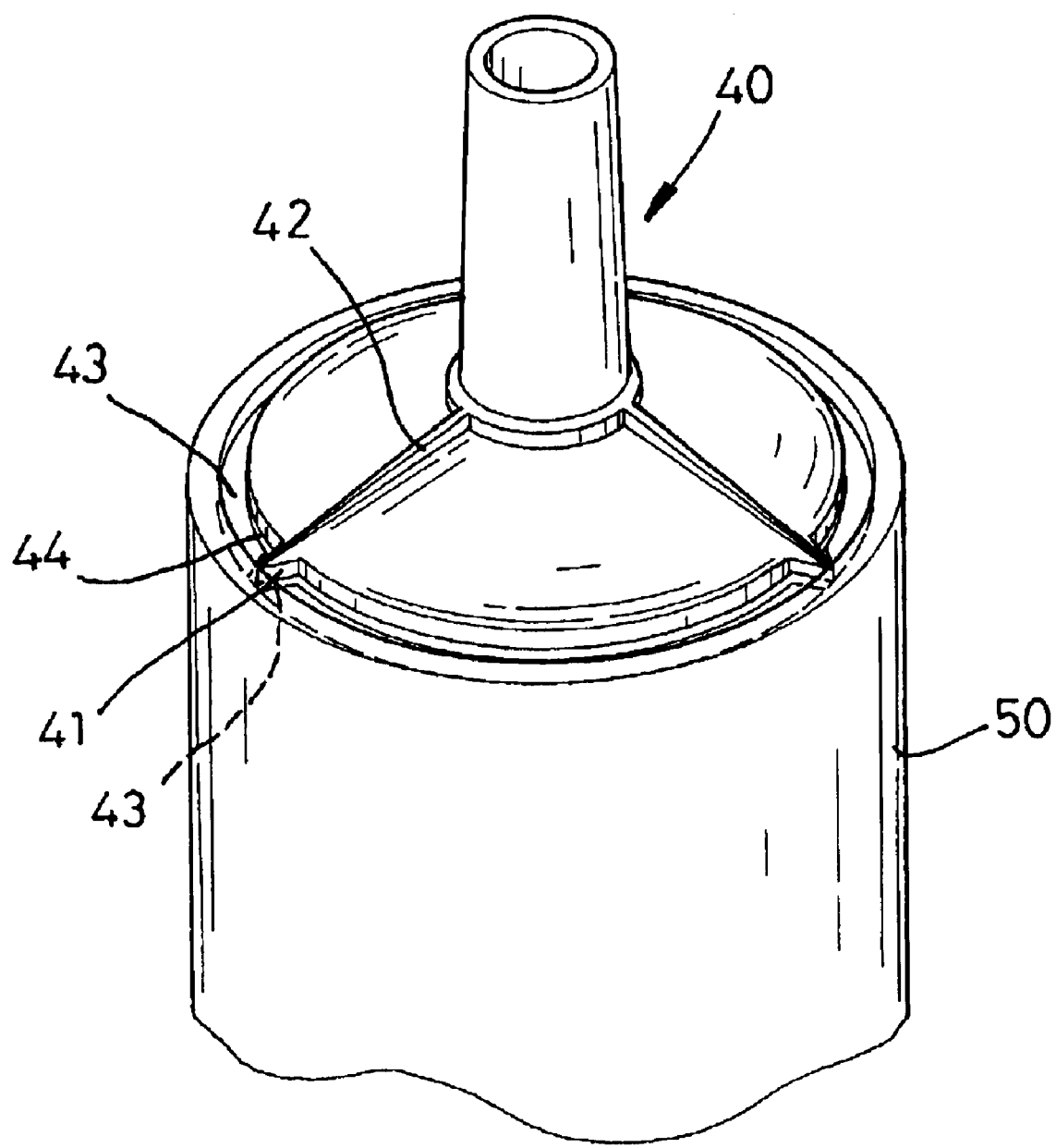
FIG. 7 is a perspective view showing another embodiment of the present invention.

With reference to FIG. 7, another embodiment of the present invention is shown, wherein the barrel (50) has a needle hub (40) integrally formed with the barrel (50).

An inner periphery of the barrel (43) integrally extends from the barrel (50). A V-shape groove formed a thin membrane (44) around the outer periphery of the needle hub (40) and connected to the inner periphery of the barrel (43).

With reference to FIG. 3, the inner periphery of the barrel (43) is thicker than that of the thin membrane (44).

The thin membrane (44) has multiple pyramidal blocks (41) extended from the hub periphery formed on atop surface of the thin membrane (44). Triangular ribs (42) extend from the outer periphery of the needle hub (40) and each triangular rib (42) corresponds to one of the pyramidal blocks (41). Multiple triangular cutouts (431) are formed on the inner periphery of the barrel (43) to correspond to the multiple pyramidal blocks (41) and are V-shape grooved with the thin membrane (44). Therefore, each of the pyramidal blocks (41) is spaced away from the inner periphery of the barrel (50).

Therefore, when the needle hub (40) is pulled backward by the plunger (not shown), the pyramidal blocks (41) tear the thin membrane (44) to completely separate the needle hub (40) from the barrel (50) to allow the needle hub (40) to be received in the barrel (50).

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A safety syringe having a barrel, a needle hub engaged with said barrel and a plunger slidably received in the barrel to engage with the needle hub so as to retract the needle hub into the barrel, wherein the improvement comprise:
   a. a V-shaped groove formed at a thin membrane surrounding the needle hub, wherein the V-shaped groove separates the needle hub and the barrel into an inner periphery of the barrel and an outer periphery of the hub, wherein the inner periphery of the barrel is thicker than the thin membrane;
   b. a plurality of pyramidal blocks extended from the outer periphery of the hub facing outward to the barrel; and,
   c. a plurality of triangular cutouts with a V-shaped groove edge defined in the inner periphery of the barrel respectively corresponding to one of the plurality of pyramidal blocks.

2. The safety syringe as claimed in claim 1, wherein the triangular cutouts edged with the V-shaped groove filled with the thin membrane.

3. The safety syringe as claimed in claim 1 further comprising a plurality of ribs extending from the outer periphery of the needle hub to respectively correspond to one of the plurality of pyramidal blocks.

4. A safety syringe having a barrel, a needle hub engaged with the barrel and a plunger slidably received in the barrel to engage with the needle hub so as to retract the needle hub into the barrel, wherein the improvement comprises:
   a. a V-shaped groove formed at a thin membrane surrounding the needle hub, wherein the V-shaped groove separates the needle hub and the barrel into an inner periphery of the barrel and an outer periphery of the hub, the inner periphery of the barrel is thicker than the thin membrane, and a plurality of pyramidal blocks extend from the outer periphery of the facing outward to the barrel;
   b. a plurality of ribs extending from the outer periphery of the needle hub to respectively correspond to one of the plurality of pyramidal blocks; and,
   c. a plurality of triangular cutouts with a V-shaped groove edge defined in the inner periphery of the barrel respectively corresponding to one of the plurality of pyramidal blocks.

5. The safety syringe as recited in claim 4, wherein the plurality of triangular cutouts edged with the V-shaped groove are filled with the thin membrane.

* * * * *